Figure 1:
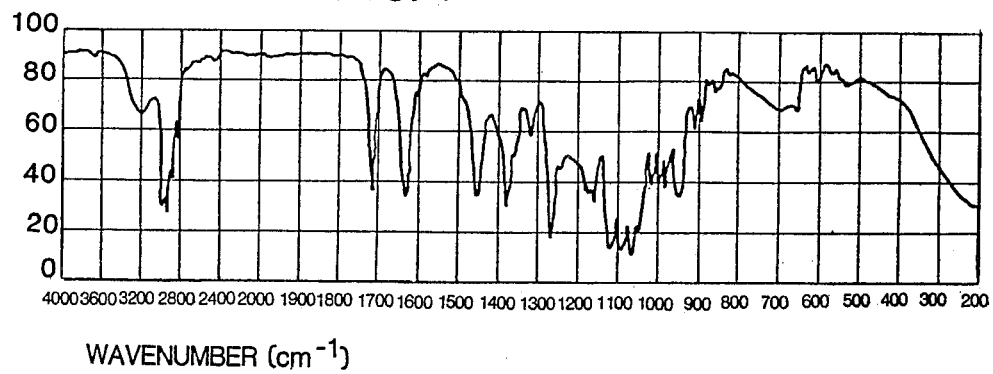

United States Patent [19]
Tsuji et al.

[11] 4,424,212
[45] Jan. 3, 1984

[54] K-41.C(2) ESTERS

[75] Inventors: Naoki Tsuji, Ashiya; Kazuo Nagashima, Neyagawa, both of Japan

[73] Assignee: Shionogi & Co., Ltd., Japan

[21] Appl. No.: 267,517

[22] Filed: May 27, 1981

[30] Foreign Application Priority Data

Jun. 13, 1980 [JP]  Japan ................................. 55-80794

[51] Int. Cl.³ ..................... A61K 31/71; A61K 35/00
[52] U.S. Cl. ..................................... 424/181; 424/121
[58] Field of Search ............... 424/181, 119, 180, 121; 536/4, 17 R; 435/119

[56] References Cited

U.S. PATENT DOCUMENTS

| | | | |
|---|---|---|---|
| 4,133,876 | 1/1979 | Hamill et al. | 424/121 |
| 4,138,481 | 2/1979 | Martin et al. | 536/4 |
| 4,269,971 | 5/1981 | Yamagishi et al. | 536/17 R |
| 4,278,663 | 7/1981 | Liu et al. | 536/4 |
| 4,303,647 | 12/1981 | Hamill et al. | 421/121 |

OTHER PUBLICATIONS

Shiro et al., J.C.S. Chem. Comm., pp. 682–683, 1978.

*Primary Examiner*—Blondel Hazel
*Attorney, Agent, or Firm*—Wenderoth, Lind & Ponack

[57] ABSTRACT

This invention relates to K-41.C(2) esters, miticidal compositions comprising K-41.C(2) esters and anti-coccidial compositions comprising K-41.C(2) esters.

13 Claims, 18 Drawing Figures

WAVENUMBER (cm$^{-1}$)

WAVENUMBER (cm$^{-1}$)

WAVENUMBER (cm$^{-1}$)

K-41.C(2) ESTERS

This invention relates to new derivatives of a polyether-type antibiotic K-41. It also provides a miticidal composition and an anti-coccidial composition containing the K-41 derivative or the salt as active ingredient. Further, it provides a method for protecting plants and animals from attack of mites and a method for protecting domestic animals and poultry from coccidiosis.

The antibiotic K-41 is produced by *Streptomyces hygroscopicus* K-41. The process for its production and its physicochemical properties have been disclosed in Japanese Patent Publication No. 21007/1977. The chemical structure was determined by X-ray analysis and nuclear magnetic resonance spectrum (J. C. S. Chem. Comm. 1978, 682–683). On the other hand, K-41 has excellent miticidal and anti-coccidial activities and can be used as the active ingredient of miticidal compositions and anti-coccidial compositions (Japanese Patent Publication (Unexamined) Nos. 53-20420 and 55-27115).

The hydroxy group at C(2) position of K-41 can be easily esterified to give K-41.C(2) ester of the general formula I:

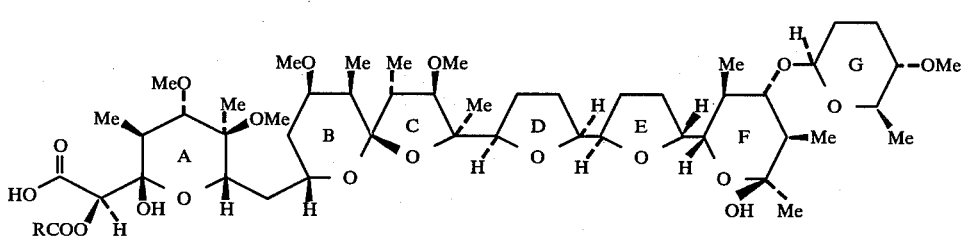

wherein Me is methyl and R is $C_{1-4}$ alkyl, phenyl-$C_{1-4}$ alkyl, $C_{1-4}$ alkoxy, phenyl-$C_{1-4}$ alkoxy, phenyl, or phenyl substituted with 1 to 3 groups selected from the group consisting of $C_{1-4}$ alkyl, $C_{1-4}$ alkoxy, halogen, and nitro.

The K-41.C(2) esters represented by the above formula I are new compounds. Both the p-bromobenzoate and p-iodobenzoate of K-41, however, have been known and are disclosed in J. A. C. S. Chem. Comm. 1978, 682–683.

In the above definition, "$C_{1-4}$ alkyl" means straight or branched $C_{1-4}$ alkyl, e.g. methyl, ethyl, propyl, isopropyl, butyl, and the like. "Phenyl-$C_{1-4}$ alkyl" means an alkyl substituted with phenyl at an optional position of the alkyl, e.g. benzyl, phenethyl and the like. "$C_{1-4}$ alkoxy" includes e.g. methoxy, ethoxy, propoxy, isopropoxy, butoxy and the like. "Phenyl-$C_{1-4}$ alkoxy" means alkoxy substituted with phenyl at any optional position, e.g. benzyloxy, phenylethoxy, phenylpropoxy and the like. Phenyl may be substituted with 1 to 3 groups selected from $C_{1-4}$ alkyl, $C_{1-4}$ alkoxy, halogen and nitro. They are exemplified by o-, m-, or p-tolyl, p-ethylphenyl, p-propylphenyl, p-isopropylphenyl, 2,4-dimethylphenyl, 2,5-dimethylphenyl, p-methoxyphenyl, p-bromophenyl, p-chlorophenyl, 3,5-dichlorophenyl, p-iodophenyl, p-nitrophenyl and the like.

The preferred R for miticidal activity if $C_{1-4}$ alkyl, $C_{1-4}$ alkoxy, phenyl-$C_{1-4}$ alkoxy, phenyl and $C_{1-4}$ alkoxyphenyl. A more preferable R is methyl, ethyl, methoxy, ethoxy, benzyloxy, phenyl and p-methoxyphenyl, especially, methyl, ethyl, and phenyl.

The preferred R for anti-coccidial activity is phenyl-$C_{1-4}$ alkoxy, phenyl and substituted phenyl, especially benzoyloxy, phenyl, $C_{1-4}$ alkyl phenyl and halogenophenyl. A more preferable R is phenyl, $C_{1-4}$ alkylphenyl, and halogenophenyl. A favorable $C_{1-4}$ alkylphenyl is tolyl, ethylphenyl, propylphenyl and isopropylphenyl, especially p-tolyl, p-ethylphenyl, p-propylphenyl and p-isopropylphenyl. A favorable halogenophenyl is chlorophenyl and bromophenyl, especially p-chlorophenyl and bromophenyl.

The pharmaceutically acceptable salts of K-41.C(2) esters can also be used in this invention. They are organic or inorganic salts commonly used in the agrochemical field such as sodium, potassium, calcium, ammonium, iron salts and the like.

K-41 Derivatives of this invention can easily be prepared by conventional esterification. Namely, acid halide reactions, acid anhydride reactions and the like are used. An acid chloride or acid anhydride having a desired acyl group may preferably be used to react with K-41. The reaction is carried out at room temperature or under cooling, if necessary, in the presence of a base, such as triethylamine, pyridine, sodium hydrogencarbonate and so on. The reaction can be carried out in an appropriate inert solvent. The solvents to be used are those usally used in esterification, for example, ethers (e.g. ether, tetrahydrofuran, dioxane and the like), hydrocarbons (e.g. benzene, toluene and the like), halogenohydrocarbons (e.g. methylene chloride and the like) and so on.

The thus-obtained K-41.C(2) esters including p-bromobenzoate and p-chlorobenzoate have miticidal and anti-coccidial activities. They are advantageously utilized as active ingredient of miticide. The effect is expected to continue for a long time when they are sprayed on field crops, since they are stable to oxidation and are decomposed slowly.

The results of tests of miticidal and anti-coccidial activites are shown below. Sodium salts of K-41.C(2) esters are used in the tests.

(1) Miticidal Activity

Test Method: Each test compound (25 mg) was dissolved in dimethyl formamide (0.5 ml). To the solution was added distilled water (30.7 ml) in a concentration of 800 ppm. The 800 ppm solution was diluted to obtain a solution of a desired concentration. A disc of 2 cm in diameter prepared from the first leaf of a kidney bean plant was placed on 0.25% agar gel plate, infested with about 15 female adults of *Tetranychus cinnabarinus* and kept at 25° C. overnight. After dead and weak adults were removed, 2 ml of a test solution in a desired concentration were applied on each disc with a sprayer. The discs were kept at 25° C. and number of dead adults were counted after 24 and 48 hours, respectively.

Test Result: The result is shown in Table 1.

TABLE 1

| Test Compound (Na salt) | Concentration ppm | Number of Test Adults | Percent of Dead Adults | |
|---|---|---|---|---|
| | | | 24 hours | 48 hours |
| Acetate | 800 | 52 | 96.2 | 98.1 |
| | 400 | 63 | 85.7 | 93.7 |
| | 200 | 61 | 80.3 | 83.6 |
| Propionate | 800 | 52 | 96.2 | 100.0 |
| | 400 | 54 | 94.4 | 96.3 |
| | 200 | 56 | 82.1 | 92.6 |
| Methoxy-carbonate | 800 | 63 | 66.7 | 83.9 |
| | 400 | 51 | 56.9 | 66.0 |
| | 200 | 53 | 41.5 | 49.1 |
| Ethoxy-carbonate | 800 | 58 | 93.1 | 98.2 |
| | 400 | 56 | 75.0 | 85.5 |
| | 200 | 61 | 50.8 | 55.7 |
| Benzyloxy-carbonate | 800 | 64 | 51.6 | 68.9 |
| | 400 | 53 | 30.2 | 34.6 |
| | 200 | 67 | 22.4 | 24.2 |
| Benzoate | 800 | 59 | 59.3 | 94.7 |
| | 400 | 63 | 31.7 | 77.6 |
| | 200 | 61 | 6.6 | 30.0 |
| p-Chloro-benzoate | 800 | 73 | 27.4 | 36.1 |
| | 400 | 63 | 22.2 | 27.0 |
| | 200 | 78 | 12.8 | 19.2 |
| p-Bromo-benzoate | 800 | 65 | 24.6 | 31.3 |
| | 400 | 78 | 10.3 | 14.5 |
| | 200 | 78 | 12.8 | 17.1 |
| p-Nitro-benzoate | 800 | 70 | 24.3 | 32.9 |
| | 400 | 65 | 13.8 | 18.8 |
| | 200 | 63 | 11.1 | 20.6 |
| p-Methoxy-benzoate | 800 | 55 | 45.5 | 69.1 |
| | 400 | 54 | 38.9 | 57.4 |
| | 200 | 63 | 22.2 | 27.0 |

(2) Anti-coccidial Activity a. Effect on *Eimeria tenella*

Test Method: The chickens, 8-day old broiler chanky, were divided into groups of three birds and infected with $5 \times 10^4$ sporulated oocysts of *Eimeria tenella* per chicken, The birds were fed with standard feed for chickens (Nihon Haigo Shiryo Co.) mixed with a test compound for 9 consecutive days from the day before infection.

On the 8th day after infection, the birds were anatomized and caecal lesions were observed. The number of bloody droppings, survival ratio, number of oocysts and caecal lesion score were observed.

Test Result: The result is shown in Table 2.

b. Effect on *Eimeria acervulina*

Test Method: The chickens, 8-day old broiler chanky, were divided into groups of three birds and infected with $5 \times 10^5$ sporulated oocysts of *Eimeria acervulina*. The birds were fed with standard feed for chickens (Nihon Haigo Shiryo Co.) mixed with a test compound for 6 consecutive days from the day before the infection. The birds were anatomized on the 5th day after infection. The number of bloody droppings, survival ratio and number of oocysts were observed. Test Result: The result is shown in Table 3.

TABLE 2

| Test Compound (Na salt) | Dose ppm | Bloody Droppings[1] | | Survival Ratio[2] | Oocyst Number[3] 8th day | Caecal Lesion Score[4] |
|---|---|---|---|---|---|---|
| | | 4th day | 5th day | | | |
| Acetate Na | 80 | − | + | 3/3 | $4 \times 10^5$ | 33 |
| Propionate | 80 | ± | ++ | 3/3 | $2 \times 10^5$ | 17 |
| Methoxy-carbonate | 80 | + | ++ | 3/3 | $3 \times 10^5$ | 33 |
| Ethoxy-carbonate | 80 | − | − | 3/3 | $3 \times 10^4$ | 3 |
| Benzyloxy-carbonate | 80 | − | − | 3/3 | $<1 \times 10^3$ | 0 |
| Benzoate | 80 | − | − | 3/3 | 0 | 0 |
| | 40 | − | − | 3/3 | $3 \times 10^5$ | 17 |
| | 20 | − | + | 3/3 | $5 \times 10^5$ | 24 |
| p-Toluate | 20 | − | − | 3/3 | $<1 \times 10^3$ | 0 |
| m-Toluate | 40 | − | − | 3/3 | 0 | 0 |
| p-Ethyl-benzoate | 20 | − | − | 3/3 | 0 | 0 |
| p-Propyl-benzoate | 40 | − | − | 3/3 | 0 | 7 |
| p-Isopropyl-benzoate | 40 | − | − | 3/3 | 0 | 0 |
| p-Chloro-benzoate | 80 | − | − | 3/3 | 0 | 0 |
| p-Bromo-benzoate | 80 | − | − | 3/3 | 0 | 0 |
| p-Nitro-benzoate | 80 | − | − | 3/3 | 0 | 0 |
| p-Methoxy-benzoate | 80 | − | − | 3/3 | $1 \times 10^4$ | 3 |
| Control (infected) | | + | +++ | 3/3 | $2 \times 10^5$ | 40 |
| Control (Non-infected) | | − | − | 3/3 | 0 | 0 |

Notes:
[1]The degrees of bloody droppings are classified for four steps; − to +++
[2]Number of surviving chickens/number of test chickens
[3]Count of oocysts existing in 1 g of feces.
[4]The degree of caecal lesions are classified to 0–40.

TABLE 3

| Test Compound (Na salt) | Dose ppm | Bloody Droppings[1] | | Survival Ratio[2] | Oocyst Number[3] 5th day |
|---|---|---|---|---|---|
| | | 4th day | 5th day | | |
| Propionate | 80 | − | − | 3/3 | $3 \times 10^5$ |
| Ethoxy-carbonate | 80 | + | ++ | 3/3 | $2 \times 10^6$ |
| Benzyloxy-carbonate | 80 | − | − | 3/3 | $6 \times 10^5$ |
| Benzoate | 80 | − | − | 3/3 | $5 \times 10^5$ |
| p-Toluate | 20 | − | − | 3/3 | $1.3 \times 10^4$ |
| p-Ethyl-benzoate | 20 | − | − | 3/3 | 0 |
| p-Propyl-benzoate | 20 | − | − | 3/3 | $1.5 \times 10^5$ |
| p-Isopropyl-benzoate | 20 | − | − | 3/3 | 0 |
| p-Chloro-benzoate | 80 | − | − | 3/3 | 0 |
| p-Bromo-benzoate | 80 | − | − | 3/3 | 0 |
| p-Nitro-benzoate | 80 | − | − | 3/3 | $5 \times 10^4$ |
| p-Methoxy-benzoate | 80 | − | − | 3/3 | $9 \times 10^4$ |
| Control (infected) | | ++ | +++ | 3/3 | $1-5 \times 10^7$ |
| Control (Non-infected) | | − | − | 3/3 | 0 |

Notes:
[1-3]See the notes in Table 2.

K-41 Derivatives of this invention have miticidal activity as shown above and can be applied to prevent and kill mites on field crops and domestic animals, including poultry, for example, Family Tetranychidae: e.g. *Tetranychus telarius, Panonychus citril, Panonychus ulmi, Eotetranychus sexmaculatus, Eotetranychus kankitus, Tetanychus viennensis, Tetranychus urticae, Bryobia praetiosa, Bryobia rubrioculus, Eotetranychus smithi, Tetranychus kanzawai* and the like, Family Tenuipalpidae: e.g. *Brevipaltus lewisi, Tenuipalpus zhizhilashviliae* and the like, Family Eriophyidae: e.g. *Aculus pelikassi, Calepitrmerus vitis* and the like, Family Acarida: e.g. *Rhiizoglyphus echinopus,* Family Ixodidae; Family Pyroglyphidae and the like.

K-41.C(2) Esters of the above formula I and the pharmaceutically acceptable salts (e.g. sodium, potassium, calcium, magnesium, ammonium, iron salts and the like) are used as the active ingredient of miticidal composition alone or as a mixture. The miticidal composition comprises a miticidally effective amount of a K-41.C(2) ester or the salt as active ingredient. The composition may contain about 0.01 weight percent to about 90 weight percents of a K-41.C(2) ester or the salt as active ingredient. A K-41.C(2) ester is mixed with suitable carriers and formulated to be emulsions, solutions, wettable powders, dust, granules, ointments, aerosols and the like. The compound is, for example, homogeneously dissolved in hydrocarbon (e.g. benzene, xylene, toluene, naphtha, and the like) or alchohol (e.g. methanol, ethanol, and the like) with suitable surfactant to obtain an emulsion or a solution. It is mixed with mineral powder (e.g. talc, clay, bentonite, pyrophyllite, diatomaceous earth and the like) and suitable surfactant or dispersant, homogenized and crushed to fine powder to give a wettable powder. The thus-prepared compositions are diluted with water to a desired concentration and sprayed. Alternatively, it may be diluted with mineral powder, homogeneously blended, crushed and used as dust. The composition can be combined with other agrochemicals, e.g. insecticides, sterilizers, herbicides, plant-growth regulators, other miticides and the like. Further, it can also be mixed with nutrients, external animal drugs, repellents and the like.

The method for protecting plants and animals from attack of mites comprises applying the composition which contains a K-41.C(2) ester or the salt as active ingredient as noted above. The miticidal compositions containing K-41.C(2) ester or the salt as active ingredient are sprayed on soil and leaves and applied to animal- and poultry-houses by residual spraying or to animal and poultry by local application in accordance with the growth of the objective mites. The amount of the composition applied to mites on plants usually ranges from about 10 g to 100 g of active ingredient per 10 ares though the amount varies depending on the subject to be applied and application season. The amount usually ranges from about 1 to 200 ppm when the composition is applied to mites being parasitic to animals.

The K-41.C(2) esters or the salts, when used as the active ingredient of anti-coccidial compositions can be used singly or as a mixture with suitable carriers utilized in this field. The composition comprises an anti-coccidially effective amount of a K-41.C(2) ester or the salt as active ingredient. Practically, it may comprise as active ingredient about 0.01 weight percent to 90 weight percent of a K-41.C(2) ester or the salt. Additionally, disintegrating agents, lubricants, stabilizers, flavorings, wetting agents, coloring agents, preservatives, aromatics and the like may be added, if necessary, to obtain powders, dusts, granules, solutions, suspensions, premixes, capsules, emulsions, tablets, and the like. Carriers are selected from those commonly used in poultry drugs, for example, water, lactose, sucrose, talc, colloidal silica, soybean brewer's grain, starch, yeast, wheat, defatted rice bran, defatted soybean, corn, wheat bran and other commercially available feed for domestic animals and poultry.

The method for protecting domestic animals and poultry from coccidiosis and treating them for it is as follows: The anti-coccidial composition can be mixed with feed or drinking water and administered. Otherwise, it can be orally administered to domestic animals and poultry without dilution. The composition is preferably applied to domestic poultry (e.g. chickens, ducks, turkeys and the like), especially chickens. Solutions, suspensions, emulsions and the like are conveniently used for mixing with feed and drinking water. Capsules and tablets are suitable for oral administration. The K-41 Derivative is added to feed in a proportion of about 0.001 to 0.05 weight percent and is mixed in drinking water in a proportion of about 0.0005 to 0.03 weight percent. It is orally administered at about 20 to 200 mg/kg body weight at a time. The dosage noted above varies depending on the applied subject, purpose, seriousness of coccidiosis and the like.

Besides, other anti-coccidial agents for domestic animal and poultry, parasiticides and the like can be mixed with the present composition, if desired.

The following examples are given solely for the purpose of illustration and are not construed as limitation of the present invention.

EXAMPLE 1

The sodium salt of K-41 (987 mg) is dissolved in dry pyridine (5 ml) and benzoyl chloride (128 μl) is added thereto at room temperature under stirring within 5 minutes. The mixture is allowed to stand for 3 hours and is evaporated after addition of some pieces of ice. The resultant colorless viscous oil is dissolved in benzene (15 ml), washed with 5% tartaric acid, water, a saturated sodium hydrogencarbonate solution, water, and a saturated sodium chloride solution successively, dried over sodium sulfonate and evaporated. The product, a colorless viscous oil is recrystallized from benzene-hexane to give sodium salt of K-41.C(2) benzoate (968 mg) as colorless crystals. (Yield 90%). Mp, 188°–190° C. (decomp.).

Anal. Calcd. for $C_{55}H_{85}O_{19}Na$: C, 61.55; H, 7.98; Na, 2.14%; Found: C, 61.72; H, 8.31; Na, 2.06%

IR spectrum: See FIG. 1.

EXAMPLE 2

The sodium salt of K-41 (987 mg) is dissolved in dry pyridine (5 ml) and acetic anhydride (104 μl) is added thereto at room temperature under stirring for 5 minutes. The mixture is allowed to stand for 4 hours and then is treated in the same manner as in Example 1. Recrystallization from benzene-hexane gives the sodium salt of K-41.C(2) acetate (916 mg). (Yield 90%). Mp. 184°–185° C. (decomp.).

Anal. Calcd. for $C_{50}H_{83}O_{19}Na$: C, 59.39; H, 8.27; Na, 2.27; Found: C, 59.29; H, 8.45; Na, 2.01

Figure 2:
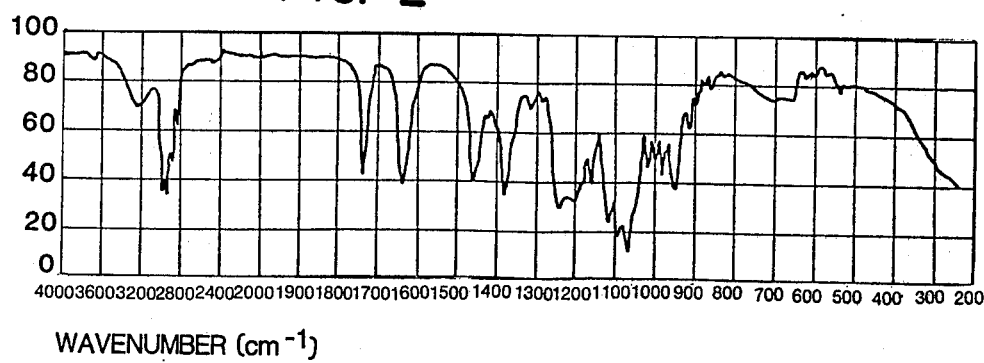

IR spectrum: See FIG. 2.

EXAMPLE 3

The sodium salt of K-41 (987 mg) is dissolved in dry pyridine (5 ml) and methyl chlorocarbonate (115 μl) is added thereto with stirring under ice-cooling within 2 hours. The mixture is kept under ice-cooling for 4 hours and then is treated in the same manner as in Example 1 to give colorless viscous oil (1.27 g). The product, crude K-41.C(2) methoxycarbonate (2.48 g) is subjected to column chromatography on silica gel and eluted with chloroform:acetonitrile (2:1), and fractions of 15 g each are obtained. Fraction Nos. 9–15 are collected and evaporated to give sodium salt of K-41.C(2) methoxycarbonate (1.62 g) as colorless powder. (Yield 79%). Mp. 172°–173° C. (decomp.).

Anal. Calcd. for $C_{50}H_{83}O_{20}Na.3H_2O$: Calcd. : C, 55.54; H, 8.30; Na, 2.13; Found: C, 55.54; H, 8.06; Na, 2.30

Figure 3:
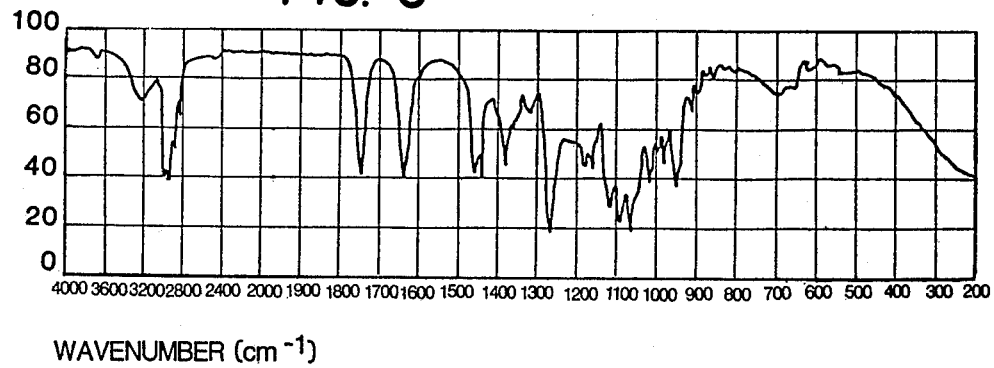

IR specrum: See FIG. 3.

EXAMPLE 4

The sodium salt of K-41 and a desired acid chloride are reacted at room temperature in the same manner as in Example 1 and evaporated. The resultant residue is purified in the same manner as in Example 1 or 3 to give the following compounds.

EXAMPLE 20

Fifteen weight percent K-41.C(2) propionate, 80 wt. % diatomaceous earth, 2 wt. % lignine sulfonate and 3 wt. % alkyl benzenesulfonate are homogeneously mixed and finely crushed to give a wettable powder, which is suitably diluted when applied.

EXAMPLE 21

Three weight percent K-41.C(2) ethoxycarbonate and 97 wt. % talc are homogeneously mixed and crushed to give a dust.

EXAMPLE 22

Figure 4:
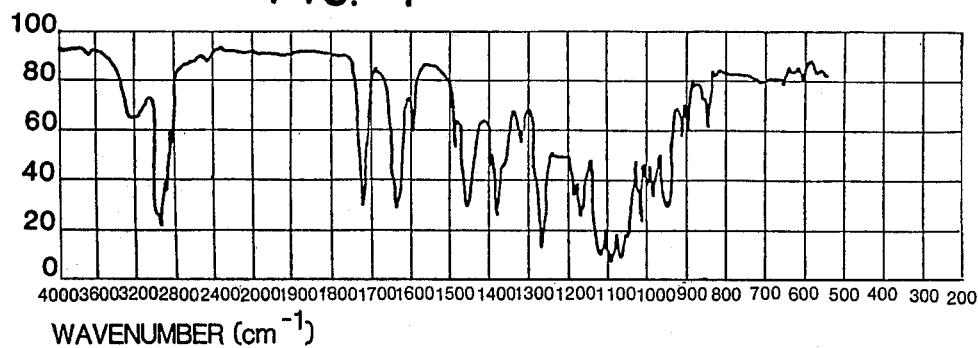
Figure 5:
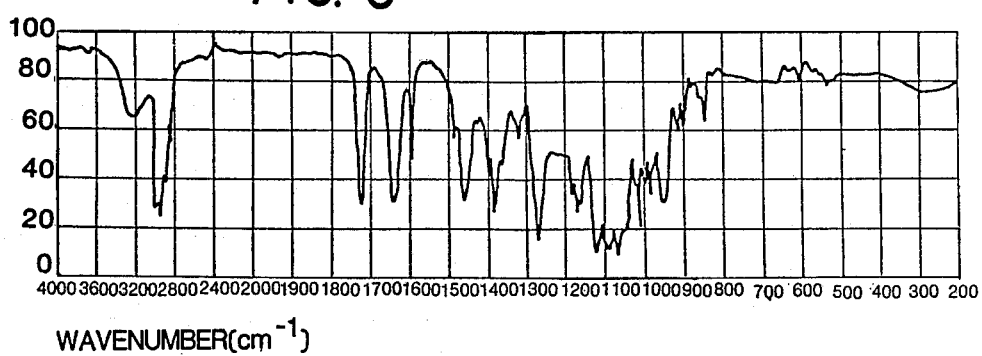
Figure 6:
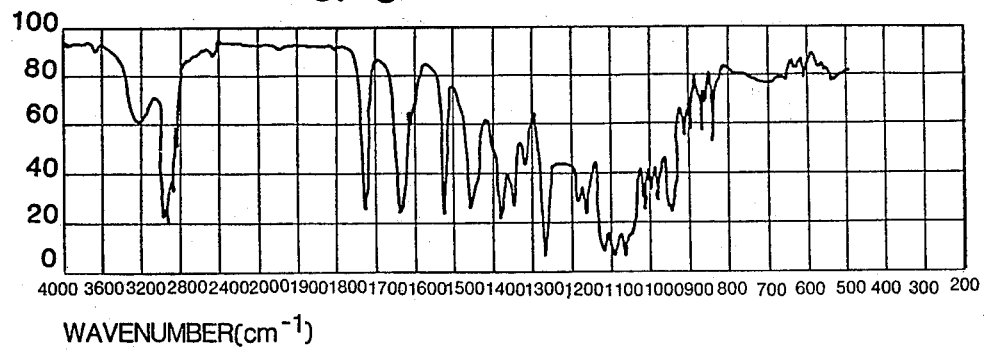
Figure 7:
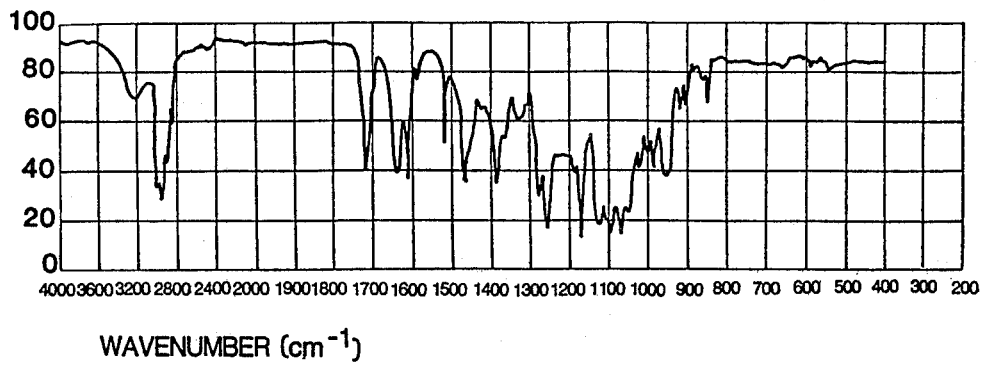
Figure 8:
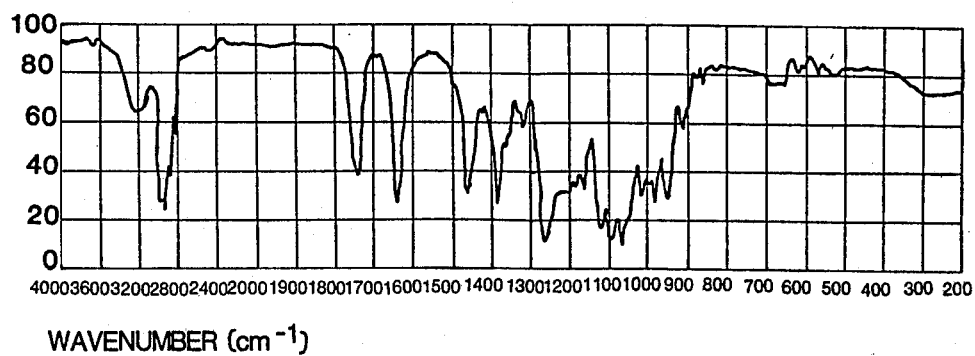
Figure 9:
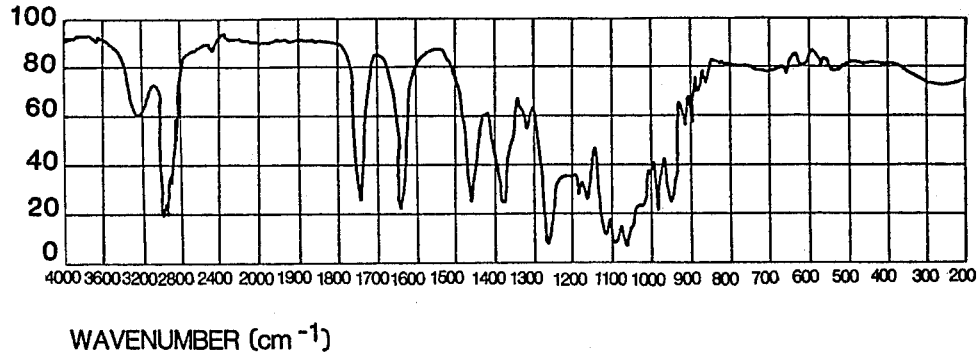
Figure 10:
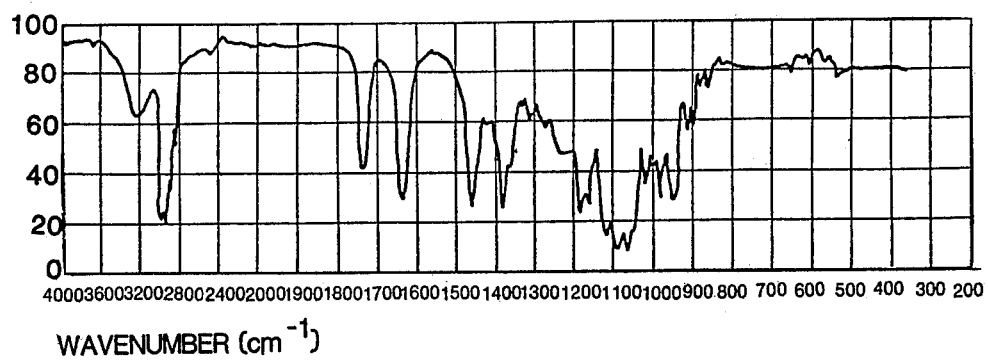
Figure 11:
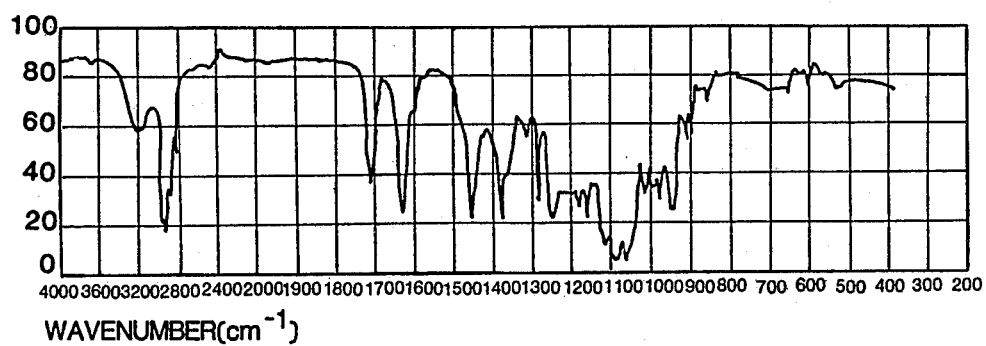
Figure 12:
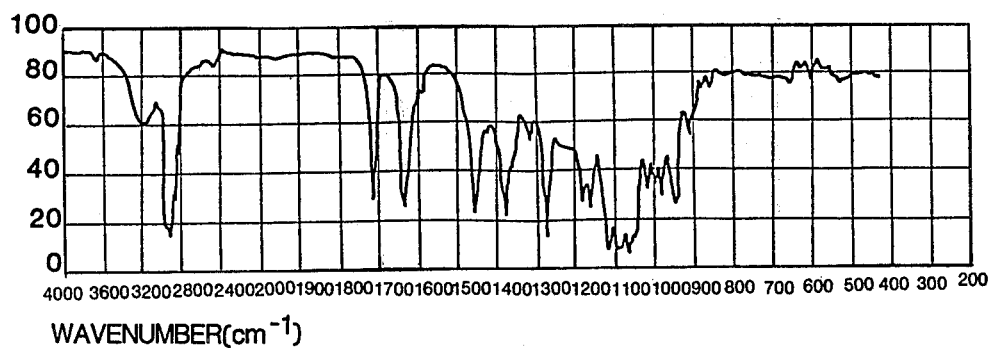
Figure 13:
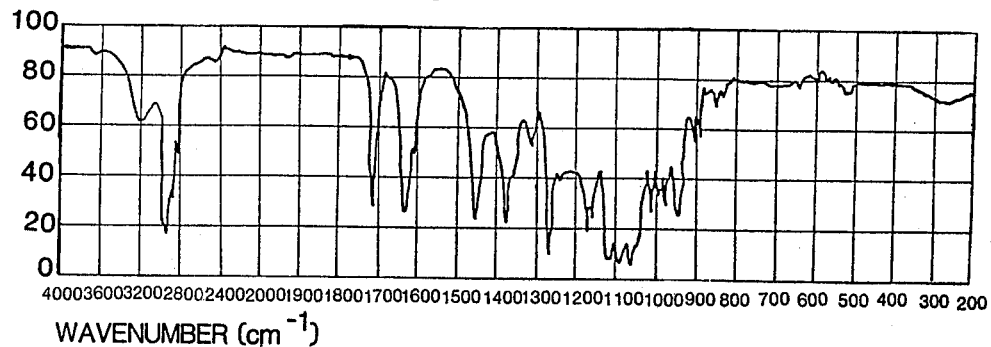
Figure 14:
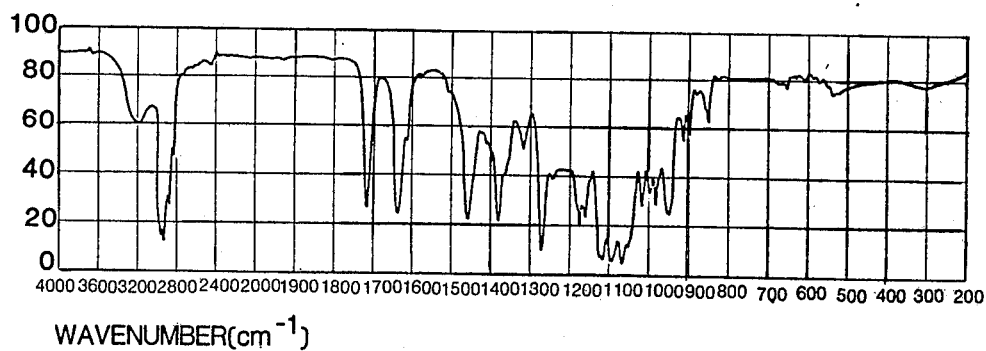
Figure 15:
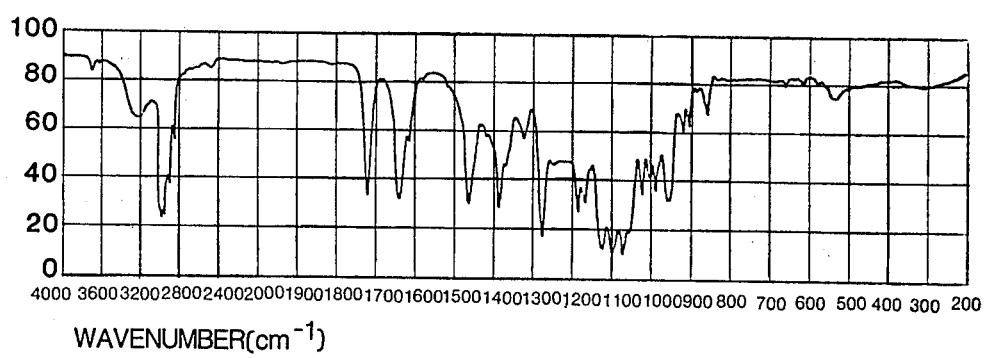
Figure 16:
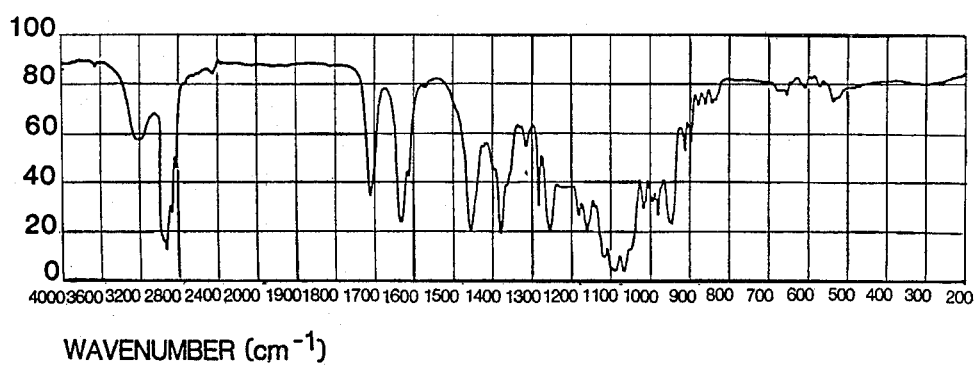
Figure 17:
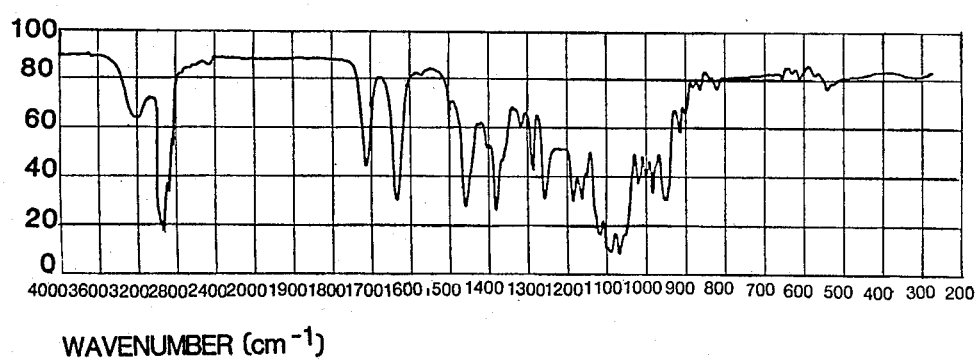
Figure 18:
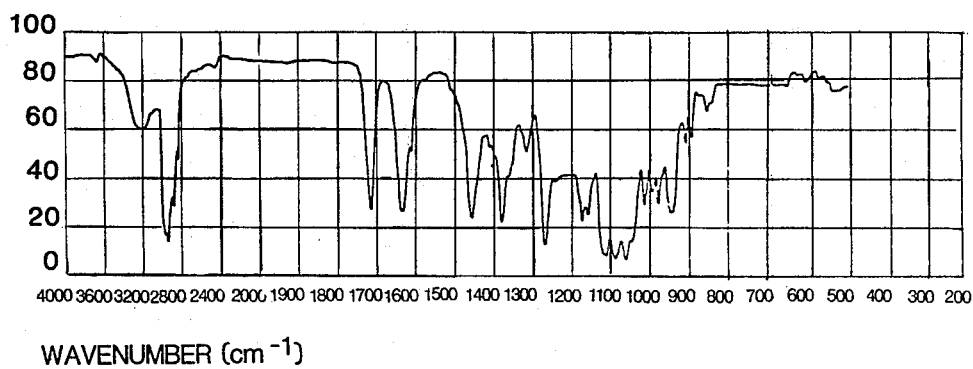

| Ex. No. | K-41.C(2) Ester | Mp.* (°C.) | Molecular formula | C | H | Na | Other | IR Spectrum |
|---|---|---|---|---|---|---|---|---|
| 4 | p-Chlorobenzoate | 189–190 (f) | $C_{55}H_{84}O_{19}ClNa$ | | | | Cl | FIG. 4 |
| | | | Calcd. | 59.63 | 7.64 | 2.08 | 3.20 | |
| | | | Found | 59.61 | 8.09 | 1.95 | 3.31 | |
| 5 | p-Bromobenzoate | 189–190 (f) | $C_{55}H_{84}O_{19}BrNa.H_2O$ | | | | | FIG. 5 |
| | | | Calcd. | 56.45 | 7.41 | 1.96 | | |
| | | | Found | 56.75 | 7.50 | 2.18 | | |
| 6 | p-Nitrobenzoate | Pale yellowish amorphous powder 192–193 (f,c) | $C_{55}H_{84}O_{21}NNa.2H_2O$ | | | | N | FIG. 6 |
| | | | Calcd. | 57.23 | 7.68 | 1.99 | 1.21 | |
| | | | Found | 57.22 | 7.56 | 1.77 | 1.16 | |
| 7 | p-Methoxybenzoate | 197–198 (f,c) | $C_{56}H_{87}O_{20}Na$ | | | | | FIG. 7 |
| | | | Calcd. | 60.96 | 7.95 | 2.08 | | |
| | | | Found | 61.01 | 8.39 | 1.91 | | |
| 8 | Benzyloxy carbonate | 163.5–164.5 (d) | $C_{56}H_{87}O_{20}Na$ | | | | | FIG. 8 |
| | | | Calcd. | 60.96 | 7.95 | 2.08 | | |
| | | | Found | 60.96 | 8.17 | 1.90 | | |
| 9 | Ethoxy carbonate | 182–183 (f,c) | $C_{51}H_{85}O_{20}Na$ | | | | | FIG. 9 |
| | | | Calcd. | 58.83 | 8.23 | 2.21 | | |
| | | | Found | 58.72 | 8.61 | 2.19 | | |
| 10 | Propionate | 188–189 (f,c) | $C_{51}H_{85}O_{19}Na.\frac{1}{2}C_6H_{14}$ | | | | | FIG. 10 |
| | | | Calcd. | 60.71 | 8.68 | 2.15 | | |
| | | | Found | 60.38 | 8.84 | 2.00 | | |
| 11 | o-Toluate | 191.5–192.5 (f,c) | $C_{56}H_{87}O_{19}Na$ | | | | | FIG. 11 |
| | | | Calcd. | 61.86 | 8.07 | 2.12 | | |
| | | | Found | 61.82 | 8.38 | 2.03 | | |
| 12 | m-Toluate | 190.5–191.5 (f,c) | $C_{56}H_{87}O_{19}Na.\frac{1}{2}C_6H_{14}$ | | | | | FIG. 12 |
| | | | Calcd. | 62.68 | 8.38 | 2.03 | | |
| | | | Found | 63.08 | 8.56 | 2.38 | | |
| 13 | p-Toluate | 190.5–191.5 (f,c) | $C_{56}H_{87}O_{19}Na$ | | | | | FIG. 13 |
| | | | Calcd. | 61.86 | 8.07 | 2.12 | | |
| | | | Found | 62.21 | 8.59 | 2.20 | | |
| 14 | p-Ethylbenzoate | 179–180 | $C_{57}H_{89}O_{19}Na.C_6H_{14}$ | | | | | FIG. 14 |
| | | | Calcd. | 63.72 | 8.74 | 1.94 | | |
| | | | Found | 63.68 | 8.79 | 2.14 | | |
| 15 | p-Isopropylbenzoate | 177 (d) | $C_{58}H_{91}O_{19}Na.\frac{1}{2}H_2O$ | | | | | FIG. 15 |
| | | | Calcd. | 61.95 | 8.25 | 2.04 | | |
| | | | Found | 61.89 | 8.43 | 2.15 | | |
| 16 | 2,4-Dimethylbenzoate | 181–182 | $C_{57}H_{89}O_{19}Na.C_6H_{14}$ | | | | | FIG. 16 |
| | | | Calcd. | 63.72 | 8.74 | 1.94 | | |
| | | | Found | 63.62 | 8.61 | 2.13 | | |
| 17 | 2,5-Dimethylbenzoate | 184–185 | $C_{57}H_{89}O_{19}Na.C_6H_{14}$ | | | | | FIG. 17 |
| | | | Calcd. | 63.72 | 8.74 | 1.94 | | |
| | | | Found | 63.95 | 8.73 | 2.24 | | |
| 18 | p-Propylbenzoate | 182–183 | $C_{58}H_{91}O_{19}Na.C_6H_{14}$ | | | | | FIG. 18 |
| | | | Calcd. | 63.97 | 8.81 | 1.91 | | |
| | | | Found | 63.91 | 8.53 | 1.94 | | |

*f = foaming,
c = coloring,
d = decomposition.

EXAMPLE 19

Ten weight percent sodium salt of K-41.C(2) acetate, 40 wt. % xylene and 50 wt. % polyoxyethylene alkyl aryl ether are homogeneously mixed to give an emulsion, which is suitably diluted and sprayed.

Ten weight percent sodium salt of K-41.C(2) benzoate and 90 wt. % lactose are well mixed to give a 10-fold diluted powder, which is diluted with feed at a concentration ranging from 0.001% to 0.05% of active ingredient when applied.

EXAMPLE 23

Twenty-five weight percent sodium salt of K-41. C(2) p-chlorobenzoate and 75 wt. % wheat flour are well blended to give a dust, which is diluted with feed at a concentration ranging from 0.001% to 0.05% of active ingredient when applied.

EXAMPLE 24

One weight percent of sodium salt of K-41.C(2) p-bromobenzoate and 99 wt. % lactose are well blended to give a 100-fold diluted powder, which is diluted with water at a concentration ranging from 0.005% to 0.03% of active ingredient.

EXAMPLE 25

Forty-five weight percent K-41.C(2) p-toluate, 12 wt. % sucrose, 15 wt. % starch, 25 wt. % talc, 2 wt. % magnesium stearate and 1 wt. % stearic acid are blended and formulated to give tablets.

EXAMPLE 26

Sodium salt of K-41.C(2) p-ethylbenzoate is used instead of K-41.C(2) benzoate in Example 22.

EXAMPLE 27

Sodium salt of K-41.C(2) m-toluate is used instead of sodium salt of K-41.C(2) benzoate in Example 24.

What we claim is:

1. A method for protecting plants and animals from the attack of mites which comprises applying a miticidally effective amount of a K-41.C(2) ester of the formula:

wherein Me is methyl and R is phenyl-$C_{1-4}$ alkyl, $C_{1-4}$ alkoxy, phenyl-$C_{1-4}$ alkoxy, phenyl, or phenyl substituted with 1 to 3 groups selected from the group consisting of $C_{1-4}$ alkyl, $C_{1-4}$ alkoxy, halogen, and nitro, or the pharmaceutically acceptable salt of said ester, as active ingredient, to said plants and animals.

2. An anti-coccidial composition which comprises an anti-coccidially effective amount of a K-41.C(2) ester of the formula:

wherein Me is methyl and R is phenyl-$C_{1-4}$ alkyl, $C_{1-4}$ alkoxy, phenyl-$C_{1-4}$ alkoxy, phenyl, or phenyl substituted with 1 to 3 groups selected form the group consisting of $C_{1-4}$ alkyl, $C_{1-4}$ alkoxy, halogen, and nitro, or the pharmaceutically acceptable salt of said ester, as active ingredient and a carrier.

3. An anti-coccidial composition which comprises as active ingredient about 0.01 weight percent to 90 weight percent of a K-41.C(2) ester of the formula:

wherein Me is methyl and R is phenyl-$C_{1-4}$ alkyl, $C_{1-4}$ alkoxy, phenyl-$C_{1-4}$ alkoxy, phenyl, or phenyl substituted with 1 to 3 groups selected from the group consisting of $C_{1-4}$ alkyl, $C_{1-4}$ alkoxy, halogen, and nitro, or the pharmaceutically acceptable salt of said ester and a carrier.

4. The anti-coccidial composition claimed in claim 2, wherein R is phenyl-$C_{1-4}$ alkoxy, phenyl, or phenyl substituted with 1 or 3 groups selected from the group consisting of $C_{1-4}$ alkyl, $C_{1-4}$ alkoxy, halogen and nitro.

5. The anti-coccidial composition claimed in claim 2, wherein R is phenyl, $C_{1-4}$ alkylphenyl and halogenophenyl.

6. The anti-coccidial composition claimed in claim 2, wherein R is tolyl, ethylphenyl, propylphenyl, or isopropylphenyl.

7. The anti-coccidial composition claimed in claim 2, wherein R is p-tolyl, p-ethylphenyl, p-propylphenyl, or p-isopropyl phenyl.

8. The anti-coccidial composition claimed in claim 2, wherein R is chlorophenyl or bromophenyl.

9. The anti-coccidial composition claimed in claim 2, wherein R is p-chlorophenyl or p-bromophenyl.

10. A method for protecting a domestic animal from coccidiosis which comprises applying the composition claimed in claim 1 to the animal.

11. The method according to claim 1 wherein said animal is poultry.

12. The composition according to claim 2 wherein R is p-ethylphenyl.

13. The method according to claim 11 wherein R is p-ethylphenyl.

* * * * *